United States Patent [19]

Freeman-McRae

[11] Patent Number: Plant 7,161

[45] Date of Patent: Feb. 20, 1990

[54] LILIUM CHINA

[75] Inventor: Judith Freeman-McRae, Boring, Oreg.

[73] Assignee: Columbia-Platte Lilies, Inc., Boring, Oreg.

[21] Appl. No.: 285,758

[22] Filed: Dec. 15, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Klarquist, Sparkman, Campbell, Leigh & Whinston

[57] ABSTRACT

A new variety of hybrid lily plant bears large clusters of flowers of excellent form and long persistence, both on the plant and as cut flowers. The flowers of the new plant are particularly characterized by their consistently and fully double form and by their soft pink coloration. This combination is completely new in the Asiatic hybrid lilies. The plant is highly resistant to disease and shows high tolerance of virus. It is an excellent garden plant. The bulbs may be precooled and forced for cut flower production. The clone is vigorous and is a good grower and propagator.

1 Drawing Sheet

BACKGROUND OF THE INVENTION

My new variety of lily plant, which I call 'China,' originated as a seedling selected from a group of seedlings growing in a cultivated area at Boring, Oreg. The seedlings resulted from breeding efforts carried on by me since 1980. The breeding efforts had as their objective the production of upright Asiatic lilies in shades of pink and cream with a truly double flower form.

I achieved the desired objective by using as the seed parent a pink seedling clone produced by crossing an unnamed upright pink clone with 'Connecticut King;' the pollen parent was a cream-colored seedling selected from the same cross. The parental seedlings were selected because of their tendency to produce occasional petaloid filaments.

The flowers of my new lily are characterized by a consistently and fully double form, a soft pink coloration, and by a delicate hairline magenta margin on the basal tepal edges of the outermost six tepals. In addition, the clone possesses to a high degree the desirable characteristics of hybrid vigor, great hardiness, and disease resistance. It possesses all of the desired characteristics of excellence of form, color, and habit. Its large flowers are produced on a single stalk. The clone is vigorous and a good grower and propagator, as observed at Boring, Oreg.

My new variety of lily plant has been asexually reproduced by me and under my direction at Boring, Oreg. Successive generations produced by bulb scale propagation, by natural propagation from bulblets, and by tissue culture propagation have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, the connection of the flower to the stem, and in particular the novel and distinctive fully double soft pink flowers.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of the Royal Horticultural Society (RHS CC), published by the Society in 1966.

The Plant

Origin: Seedling.

*Seed parent.*—Pink seedling selected from unnamed upright pink seedling×'Connecticut King,' with petaloid filaments.

*Pollen parent.*—Cream seedling selected from unnamed upright pink seedling×'Connecticut King,' with petaloid filaments.

Commercial classification: Hybrid Lilium clone.

Horticultural classification: Division 1-A, upright Asiatic hybrid lily, according to the Horticultural Classification of Lilies, Royal Horticultural Society of London.

Form: Single stem, erect and stately.

Height: 75 to 100 cm from bulbs in their second year after scale propagation.

Growth: Vigorous and upright.

Foliage quantity: Abundant.

Size of leaf: 10 to 12 cm long×1 to 2 cm wide; the leaves are slightly shorter and broader at the top of the stem.

Shape of leaf: Lanceolate (pointed).

Texture: Leathery and glossy.

Color: Deep green, lighter on lower side.

Bulb size: Any size, ranging to 25 cm circumference commercially.

Bulb color: White.

The Bud

Form: Obtuse, ovoid, and long.

Size: 8 to 9 cm long and 5–8 cm in circumference just prior to opening.

Opening: Bud opens slowly, in response to morning light; this takes about one hour.

Color: Soft pink (RHS CC Red-Purple 65 D) shading into cream at base; midribs are slightly deeper pink. Color is intensified by cool temperatures.

Peduncle: Averages 4 cm, but it may elongate if light levels are too low or if bulbs have been improperly stored prior to commercial forcing. Color is dark green with plum overlay.

The Flower

Blooming habit: Annually in midseason; flowers once and profusely.

Size: Large flowers are 16 to 19 cm in diameter; the outer tepals are 2 to 2.5 cm wide, the next circle of tepals are 2.5–3.0 cm wide, and the third and occasionally fourth ring of tepals averages 2 to 2.5 cm wide.

Borne: In a single racemic inflorescence producing 6 to 10 buds from a bulb 15 to 18 cm in circumference.

Shape: First opens in cup shape, which flattens as tepals recurve by second day.

Tepalage: 9 to 12 imbricated tepals. The innermost 3 to 6 tepals are derived from the filaments, and the innermost 3 tepals occasionally revert to form sterile (antherless) soft pink filaments.

Tepal color: Flowers are distinguished by their soft pink color pattern. The base of the tepals is RHS CC Red-Purple 65 C-D, shading into RHS CC 65 B at the tips. The color is produced by anthocyanin pigments which are affected by light levels and temperature, so that the pink will intensify to RHS 65 A or even 66 D under cool temperatures and high light intensities. High light levels associated with high temperatures will degrade the pigment and cause the flowers to become a much softer pink. Very low light levels inhibit anthocyanin formation and cause a lighter flower color. The nectary furrows are soft green, and their margins are edges with short frosty white hairs.

Tepal spotting: The basal third of each tepal carries 15–20 small magenta (RHS CC Red Purple 71 A-B) spots. The basal two-thirds of each tepal has a hairline margin of magenta color exactly matching the spotting color.

Tepal longevity: Tepals stay on stems about three weeks.

Pedicel length: Most of the pedicels are 5 to 8 cm long, but a few may reach 10 cm.

Pedicel color: Dark green with plum overlay.

Pedicel form: Sturdy and ascending up to 45 degrees from the horizontal. Occasional secondary buds.

Color changes: Flower color may change because of changes in temperature and lighting as the flower ages, as described under flower color.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut flower.

The Reproductive Organs

Stamens: The stamens have mutated to form the additional tepals; there may be 2 to 3 cream or soft pink sterile (antherless) filaments in the center of the flower.

Pistil: One in number, 5 cm long.

Stigma: Soft green with light plum overlay.

Characteristics of ovary: Characteristic of genus Lilium.

The Fruit

Fertility: Bears viable seed.

Shape: Ovoid.

Color at maturity: Soft brown, sometimes overlaid with soft plum.

My new variety of Asiatic hybrid lily most nearly resembles 'Ruffles,' but it has fully double flowers which are soft pink rather than white, more and smaller spots than 'Ruffles,' and it is taller than 'Ruffles.'

I claim:

1. A new and distinctive variety of Asiatic hybrid lily plant substantially as herein shown and described, characterized by its high resistance to disease; its tolerance of virus; its vigorous growth and rapid natural propagation; and in particular by its unusual consistently and completely double flowers with their hairline magenta tepal margins. This color pattern and double flower form are unique among Asiatic hybrid lilies.

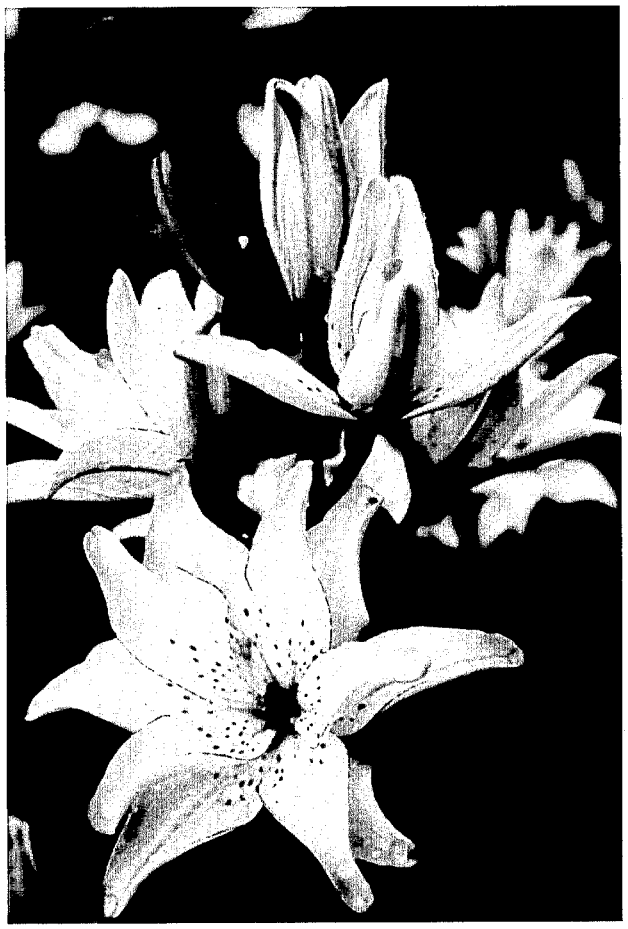

* * * * *